(12) United States Patent
Forthofer et al.

(10) Patent No.: US 12,144,712 B2
(45) Date of Patent: Nov. 19, 2024

(54) MATERIAL INCLUDING CHANNEL FOR IMPROVED FLUID DISTRIBUTION

(71) Applicant: Kimberly-Clark Worldwide, Inc., Neenah, WI (US)

(72) Inventors: Marsha R. Forthofer, South Burlington, VT (US); Karen Goeders, Alpharetta, GA (US); Wing-Chak Ng, Roswell, GA (US); Sridhar Ranganathan, Suwanee, GA (US)

( * ) Notice: Subject to any disclaimer, the term of this patent is extended or adjusted under 35 U.S.C. 154(b) by 18 days.

(21) Appl. No.: 17/606,824

(22) PCT Filed: Apr. 30, 2019

(86) PCT No.: PCT/US2019/029910
§ 371 (c)(1),
(2) Date: Oct. 27, 2021

(87) PCT Pub. No.: WO2020/222801
PCT Pub. Date: Nov. 5, 2020

(65) Prior Publication Data
US 2022/0202630 A1  Jun. 30, 2022

(51) Int. Cl.
*A61F 13/53* (2006.01)
*A61F 13/532* (2006.01)
(Continued)

(52) U.S. Cl.
CPC .......... *A61F 13/532* (2013.01); *A61F 13/534* (2013.01); *A61F 13/53756* (2013.01); *A61F 2013/53778* (2013.01)

(58) Field of Classification Search
CPC .... A61F 13/532; A61F 13/534; A61F 13/537; A61F 13/53704; A61F 13/53717;
(Continued)

(56) References Cited

U.S. PATENT DOCUMENTS 5,268,229 A   12/1993  Phillips et al.
5,427,838 A    6/1995  Yamamoto et al.
(Continued)

FOREIGN PATENT DOCUMENTS

AU   2015392739 A1   11/2017
CN      203017205 U    6/2013
(Continued)

OTHER PUBLICATIONS

Landeryou, M.A. et al., "Mapping liquid distribution in absorbent incontinence products", Sage Journals, Apr. 1, 2003, http://journals.sagepub.com/doi/abs/10.1243/095441103322060703.
(Continued)

*Primary Examiner* — Catharine L Anderson
(74) *Attorney, Agent, or Firm* — KIMBERLY-CLARK WORLDWIDE, INC.

(57) ABSTRACT

A material for distributing fluid can include a first side edge, a second side edge, a first end edge, and a second end edge. The material can include a first surface and a second surface opposite from the first surface. The material can be liquid impermeable and at least one of the first surface and the second surface include at least one channel. The channel can include a channel width, a channel length, and a channel depth. The channel width can be from 0.1 mm to 2.5 mm. The channel depth can be configured such that the channel does not extend completely through the material.

20 Claims, 6 Drawing Sheets

(51) Int. Cl.
*A61F 13/534* (2006.01)
*A61F 13/537* (2006.01)

(58) Field of Classification Search
CPC ........ A61F 13/53756; A61F 2013/5317; A61F 2013/53778
See application file for complete search history.

(56) References Cited

U.S. PATENT DOCUMENTS

| | | | |
|---|---|---|---|
| 5,451,219 | A | 9/1995 | Suzuki et al. |
| 5,514,120 | A * | 5/1996 | Johnston ........... A61F 13/53704 604/385.101 |
| 5,728,446 | A | 3/1998 | Johnston et al. |
| 6,454,750 | B1 | 9/2002 | Vogt et al. |
| 6,575,948 | B1 * | 6/2003 | Kashiwagi ........ A61F 13/47218 604/385.101 |
| 6,610,038 | B1 * | 8/2003 | DiPalma ............. A61F 13/4702 604/385.12 |
| 7,378,568 | B2 | 5/2008 | Thomas et al. |
| 8,101,815 | B2 | 1/2012 | Kaneko et al. |
| 9,610,561 | B2 | 4/2017 | Addiego et al. |
| 2006/0122572 | A1 | 6/2006 | Suarez |
| 2012/0136329 | A1 | 5/2012 | Carney |
| 2018/0021187 | A1 | 1/2018 | Nishikawa et al. |
| 2018/0303682 | A1 | 10/2018 | Nebigil |

FOREIGN PATENT DOCUMENTS

| | | |
|---|---|---|
| CN | 203970682 U | 12/2014 |
| EP | 0124365 B1 | 10/1986 |
| EP | 0536308 B1 | 2/1994 |
| EP | 0359501 B1 | 12/1994 |
| EP | 0596038 B1 | 3/1997 |
| EP | 0591647 B1 | 7/2000 |
| EP | 1005305 B1 | 10/2003 |
| EP | 1551344 B1 | 1/2009 |
| JP | 2015066377 A | 4/2015 |
| JP | 2019063323 A | 4/2019 |
| WO | 2003003959 A1 | 1/2003 |
| WO | 2019066915 A1 | 4/2019 |

OTHER PUBLICATIONS

Preservation Equipment, Absorbent Pads, Preservationequipment.com, https://www.preservationequipment.com/Catalogue/Disaster-Cleaning/Absorbent-Products/Absorbent-Pads-for-commercial-spills.

NPTEL, "Fibres For Medical Applications", http://nptel.ac.in/courses/116102006/17.

* cited by examiner

MATERIAL INCLUDING CHANNEL FOR IMPROVED FLUID DISTRIBUTION

TECHNICAL FIELD

The present disclosure relates to materials including at least one channel that help improve fluid distribution. More specifically, the present disclosure relates to materials including at least one channel that form part of an absorbent assembly such that the material can help improve fluid distribution in the absorbent assembly.

BACKGROUND OF THE DISCLOSURE

A primary function of personal care absorbent articles is to absorb and retain body exudates such as urine, fecal material, blood, and menses. An additional desired performance characteristic of absorbent care articles is to provide a dry feel to the wearer. The most basic design of such absorbent articles include a bodyside liner, an outer cover, and an absorbent body disposed between the bodyside liner and the outer cover. Body exudates are often initially received in an absorbent article in a specific insult region, and depending on the particular absorbent article and the wearer, the absorbent article may receive multiple insults while the wearer is wearing the same absorbent article. If the absorbent article is not properly intaking and/or distributing the insults of body exudates, leakage of the absorbent article may occur near the leg, top front, or top back areas of the absorbent article. Lack of proper intake and/or distribution of body exudates may also lead to a wet feel to the wearer.

Attempts to alleviate leakage include the use of physical barriers, such as leg containment flaps and/or elastic leg gathers, and waist containment members, which can provide a barrier to exudates from leaking from the absorbent article while the insult has time to be distributed through the absorbent assembly. However, such systems add additional complexity and cost to the absorbent article, and may not address the wetness the wearer may experience from any pooled exudates that are contained, but waiting to be distributed through the absorbent assembly Other known techniques that try to address this problem are to provide one or more acquisition layers, commonly referred to as a surge layer, above the absorbent body to help slow and distribute the exudates to the absorbent body. However, improvements can still be made to these systems, especially for enhanced performance in subsequent insults.

Thus, there remains a need for improvements in exudate distribution throughout the absorbent assembly. Additionally, there remains a need for improvements in exudate distribution of second or subsequent insults to an absorbent article.

SUMMARY OF THE DISCLOSURE

In one embodiment, a material can include a first side edge, a second side edge opposite from the first side edge, a first end edge, and a second end edge opposite from the first end edge. The material can further include a first surface and a second surface opposite from the first surface. A distance between the first surface and the second surface can define a thickness of the material. The material can be liquid impermeable and at least one of the first surface and the second surface can include at least one channel. The at least one channel can include a channel width. The channel width can be from 0.1 mm to 2.5 mm. The at least one channel can also include a channel length and a channel depth. The channel depth can be configured such that the channel does not extend completely through the material.

In another embodiment, an absorbent assembly can include an absorbent body. The absorbent body can include absorbent material, a first end edge, a second end edge opposite from the first end edge, a pair of longitudinal side edges, a top surface, and a bottom surface opposite from the top surface. The absorbent assembly can also include a material that can be liquid impermeable. The material can include a first side edge, a second side edge opposite from the first side edge, a first end edge, a second end edge opposite from the first end edge, a first surface, and a second surface opposite from the first surface. A distance between the first surface and the second surface can define a thickness of the material. The first surface can include at least one channel. The at least one channel can include a channel width, a channel length, and a channel depth. The channel depth can be configured such that the channel does not extend completely through the material.

In yet another embodiment, an absorbent article can include a bodyside liner. The absorbent article can also include an absorbent body. The absorbent body can include absorbent material, a front end edge, and a rear end edge. The rear end edge can be opposed from the front end edge. The absorbent body can also include a pair of longitudinal side edges. The absorbent article can also include a material. The absorbent body can be disposed between the bodyside liner and the material. The material can be liquid impermeable and can include a first side edge and a second side edge. The second side edge can be opposite from the first side edge. The material can also include a first end edge, a second end edge opposite from the first end edge, a first surface, and a second surface opposite from the first surface. A distance between the first surface and the second surface can define a thickness of the material. The first surface can include a plurality of channels. The plurality of channels can each include a channel width, a channel length, and a channel depth. The channel depth can be configured such that the channel does not extend completely through the material.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
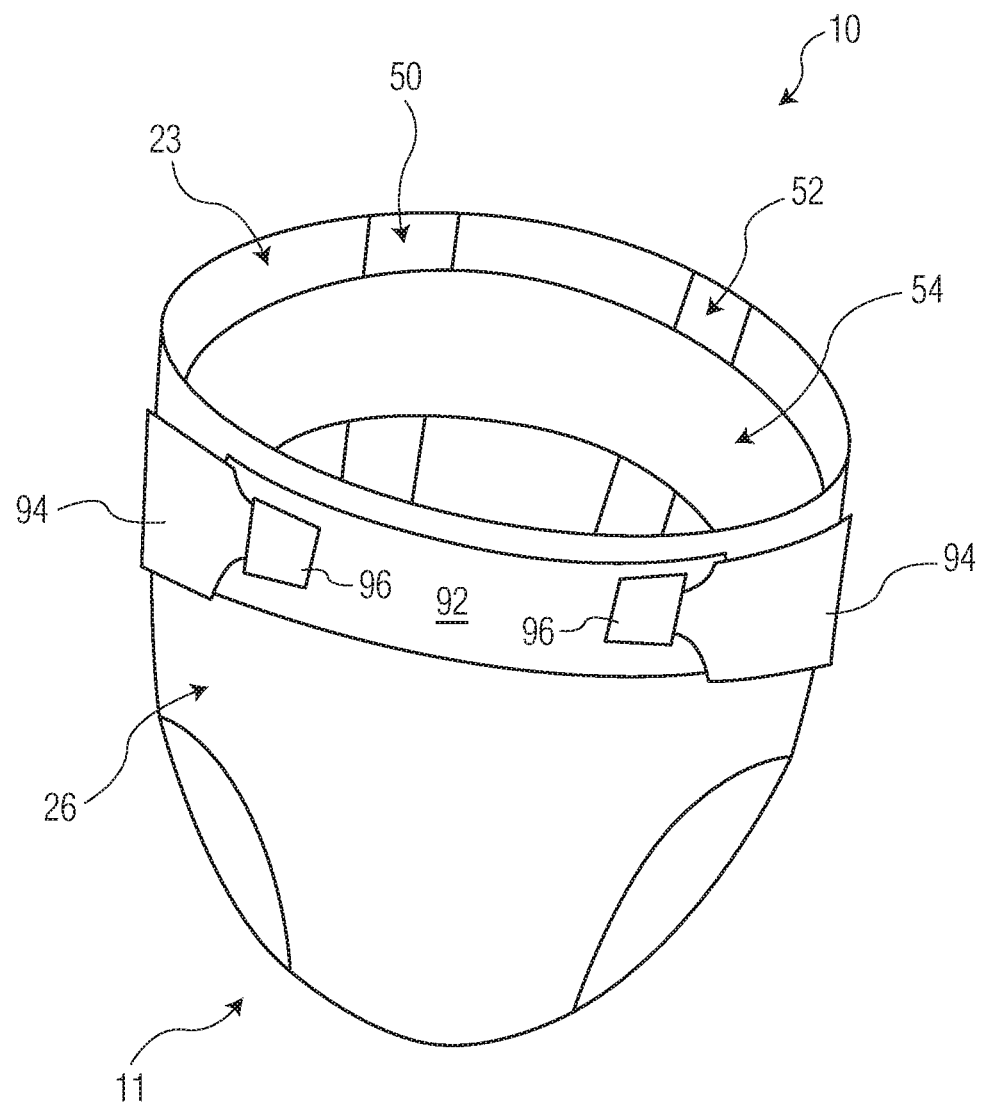
FIG. 1 is front perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards a distribution material 70 that includes at least one channel 72, and preferably a plurality of channels 72, that help distribute fluid. The distribution material 70 can be used in a variety of applications and end uses. For example, the distribution material 70 can form a component of an absorbent assembly 44 and/or a component of an absorbent article 10. In such configurations, the channel(s) 72 in the distribution material 70 can help distribute fluid to the absorbent body 34 in the absorbent assembly 44 to provide a more efficient distribution and use of the absorbent material in the absorbent body 34 and reducing the likelihood of leaks from the absorbent article 10. The increased effectiveness of the distribution of fluid in the absorbent assembly 34 can provide the additional advantages of potentially reducing the amount of absorbent material used in the absorbent body 34, and thus, potentially reducing the size of the absorbent body 34 which may help provide improved fit and/or flexibility to the absorbent article 10. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 2:
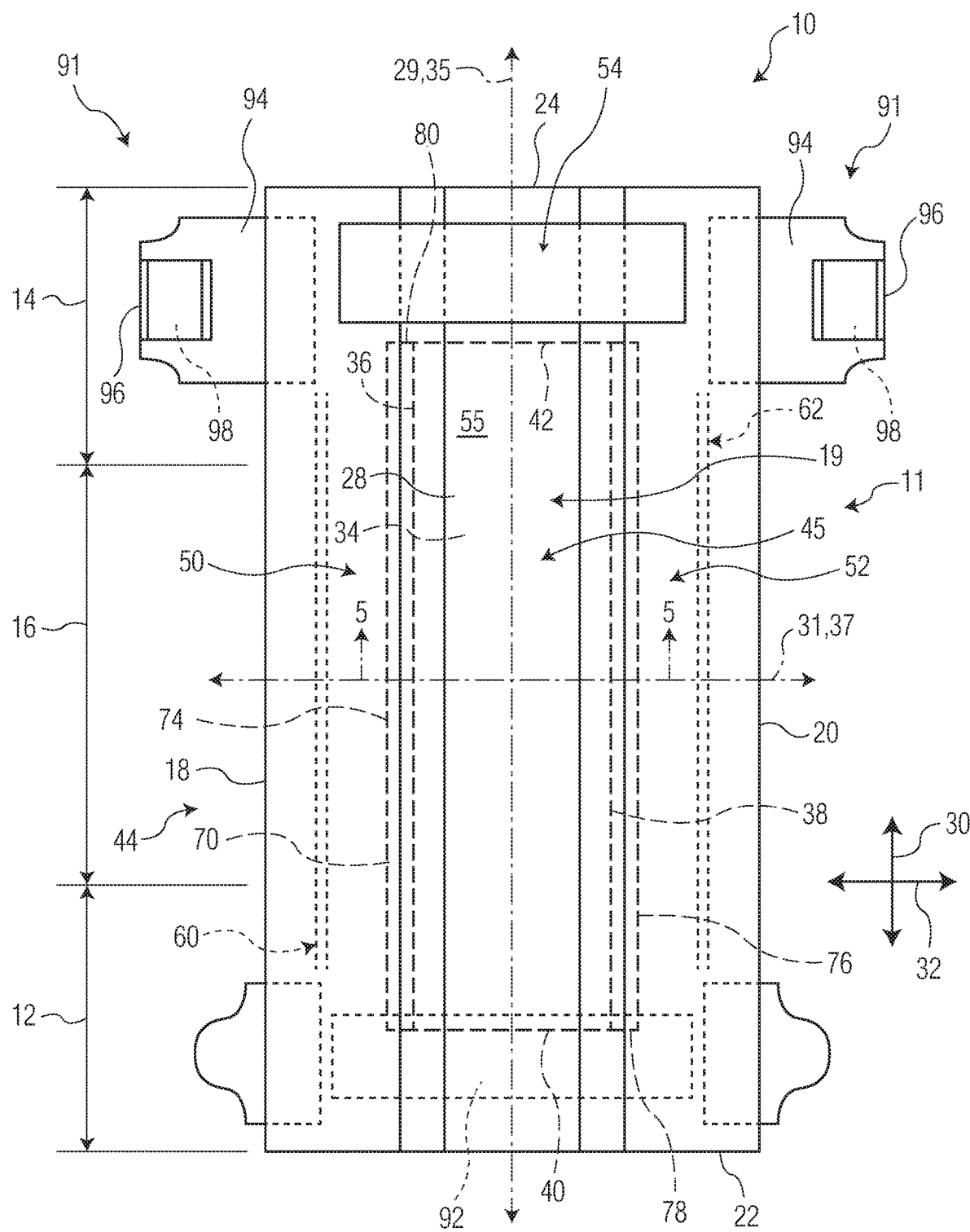
FIG. 2 is a top plan view of the absorbent article of FIG. 1 in a stretched, laid flat, unfastened condition.

Absorbent Article:

Referring to FIGS. 1 and 2, a non-limiting illustration of an absorbent article 10, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1 and 2 can include a chassis 11. The absorbent article 10 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region.

As illustrated in FIG. 2, the absorbent article 10 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10 illustrated in FIG. 2. In other embodiments, the longitudinal side edges 18, 20 can be curved between the front waist edge 22 and the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10 that, when worn, is positioned between the legs of the wearer and can partially cover the lower torso of the wearer. The waist edges, 22 and 24, of the absorbent article 10 are configured to encircle the waist of the wearer and together define a central waist opening 23 (as labeled in FIG. 1) for the waist of the wearer. Portions of the longitudinal side edges 18, 20 in the crotch region 16 can generally define leg openings for the legs of the wearer when the absorbent article 10 is worn.

The absorbent article 10 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28. The absorbent body 34 can have a pair longitudinal side edges, 36 and 38, which, in an embodiment, can form portions of the longitudinal side edges, 18 and 20, respectively, of the absorbent article 10. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12 and can be referred to as a front end edge 40 of the absorbent body 34. In some embodiments, the second end edge 42 can be in the rear waist region 14 and can be referred to as a rear end edge 42 of the absorbent body 34. In an embodiment, the absorbent body 34 can have a length and width that are the same as or less than the length and width of the absorbent article 10.

Figure 5:
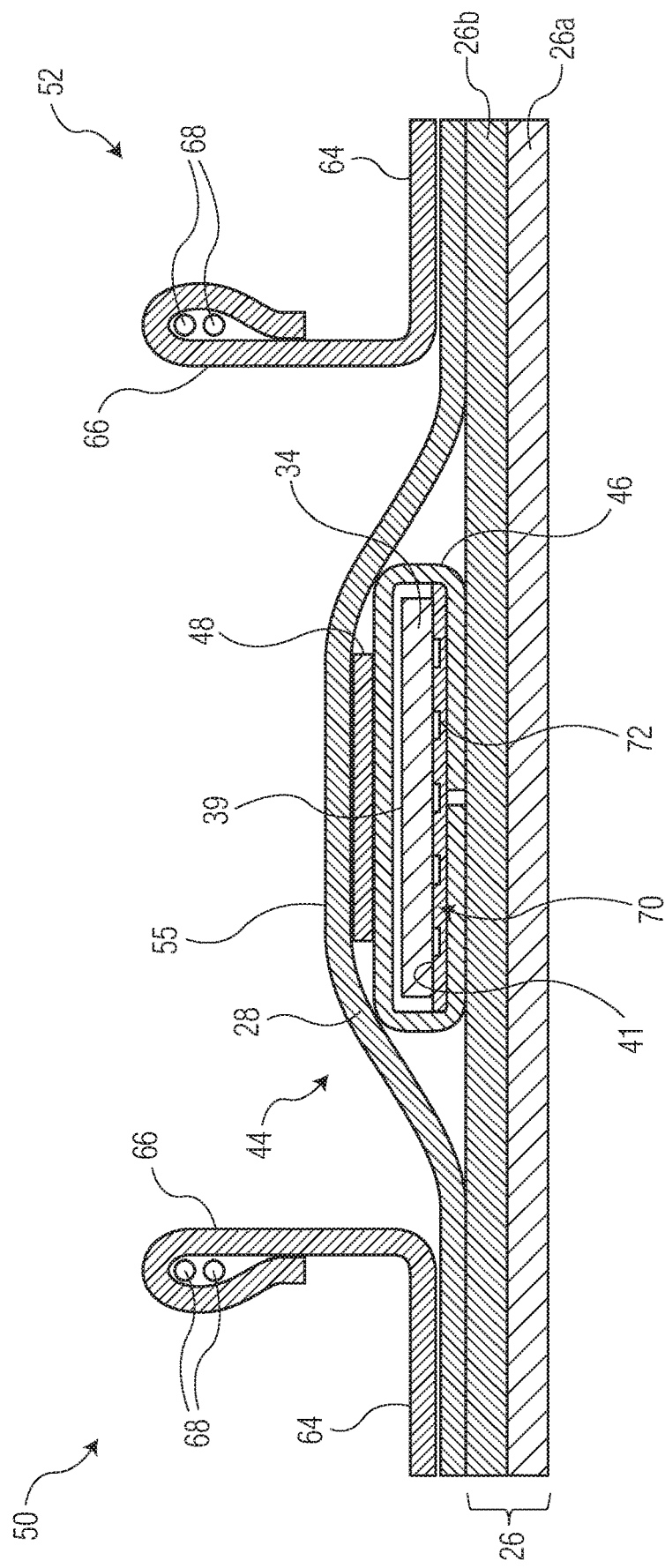
FIG. 5 is a cross-section taken along line 5-5 from FIG. 2.

The absorbent body 34 can form part of an absorbent assembly 44. The absorbent assembly 44 can also include a fluid transfer layer 46 (shown in FIG. 5) and a fluid acquisition layer 48 (shown in FIG. 5) between the bodyside liner 28 and the absorbent body 34. In some embodiments, if a fluid transfer layer 46 is present, the acquisition layer 48 can be between the bodyside liner 28 and the fluid transfer layer 46 as is known in the art. The absorbent assembly 44 can also include a spacer layer (not shown) disposed between the absorbent body 34 and the outer cover 26 as is known in the art. The absorbent assembly 44 can also include a distribution material 70. In some preferred embodiments, such as shown in FIG. 5, the distribution material 70 can be disposed between the absorbent body 34 and the outer cover 26. The distribution material 70 can include one or more channels 72 that can help distribute the fluid, such as urine or other bodily fluids, to the absorbent body 34, as will be further discussed in detail below. The absorbent assembly 44 can include other components in some embodiments. It is also contemplated that some embodiments may not include a fluid transfer layer 46, and/or an acquisition layer 48, and/or a spacer layer.

The absorbent article 10 can be configured to contain and/or absorb liquid, solid, and semi-solid body exudates discharged from the wearer. In some embodiments, a pair of containment flaps 50, 52 can be configured to provide a barrier to the lateral flow of body exudates. In some embodiments, the absorbent article 10 can include a waist containment member 54. The waist containment member 54 can be disposed in the rear waist region 14 of the absorbent article 10. Although not depicted herein, it is contemplated that the waist containment member 54 can be additionally or alternatively disposed in the front waist region 12 of the absorbent article 10.

The absorbent article 10 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10. The leg elastic members 60, 62 can be parallel to the longitudinal axis 29 as shown in FIG. 2 or can be curved as is known in the art. The leg elastic members 60, 62 can provide elasticized leg cuffs.

Additional details regarding each of these elements of the absorbent article 10 described herein can be found below and with reference to the FIGS. 1 through 5.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 410. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer 26a and an inner layer 26b (each shown in FIG. 5) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer 26a of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 26a of an outer cover 26 can be a 20 gsm spunbond polypropylene non-woven web. The outer layer 26a may also be constructed of the same materials from which the bodyside liner 28 can be constructed as described herein.

The liquid impermeable inner layer 26b of the outer cover 26 (or the liquid impermeable outer cover 26 where the outer cover 26 is of a single-layer construction) can be either vapor permeable (i.e., "breathable") or vapor impermeable. The liquid impermeable inner layer 26b (or the liquid impermeable outer cover 26 where the outer cover 26 is of a single-layer construction) can be manufactured from a thin plastic film. The liquid impermeable inner layer 26b (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

In some embodiments, the outer cover 26 can be configured such that the distribution material 70 as described herein forms a portion of the outer cover 26. For example, in some embodiments the distribution material 70 as described herein can be the liquid impermeable inner layer 26b of the outer cover 26 (or the liquid impermeable outer cover 26 where the outer cover 26 is of a single-layer construction). In these configurations, the outer cover 26 can be configured to include one or more channels 72 that can help distribute fluid to the absorbent body 34, as further discussed in below with respect to the section on the distribution material 70.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10. The absorbent body 34 can have a longitudinal axis 35 and a lateral axis 37. The length of the absorbent body 34 can be measured along the longitudinal axis 35 of the absorbent body 34 and the width of the absorbent body 34 can be measured along the lateral axis 37 of the absorbent body 34.

The absorbent body 34 can have a pair of longitudinal side edges 36, 38, a first end edge 40 and a second end edge 42 opposite from the first end edge 40. In some embodiments, the first end edge 40 of the absorbent body 34 can be disposed in the front waist region 12 and the second end edge 42 of the absorbent body 34 can be disposed in the rear waist region 14. As illustrated in FIG. 5, the absorbent body 34 can include a top surface 39 and a bottom surface 41 that is opposite from the top surface 39. The absorbent body 34 can be disposed in the absorbent article 10 such that the top surface 39 of the absorbent body 34 can be closer to the bodyside liner 28 than the bottom surface 41 of the absorbent body 34 is to the bodyside liner 28, and such that the bottom surface 41 of the absorbent body 34 can be closer to the outer cover 26 than top surface 39 of the absorbent body 34 is to the outer cover 26.

The absorbent body 34 includes absorbent material. In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer, can be positioned between the absorbent body 34 and the outer cover 26. In some embodiments, a distribution material 70 can be disposed between the absorbent body 34 and the outer cover 26. The absorbent body 34 can be bonded to the distribution material 70 and/or the fluid transfer layer 46 and/or the spacer layer (if present).

Figure 3:
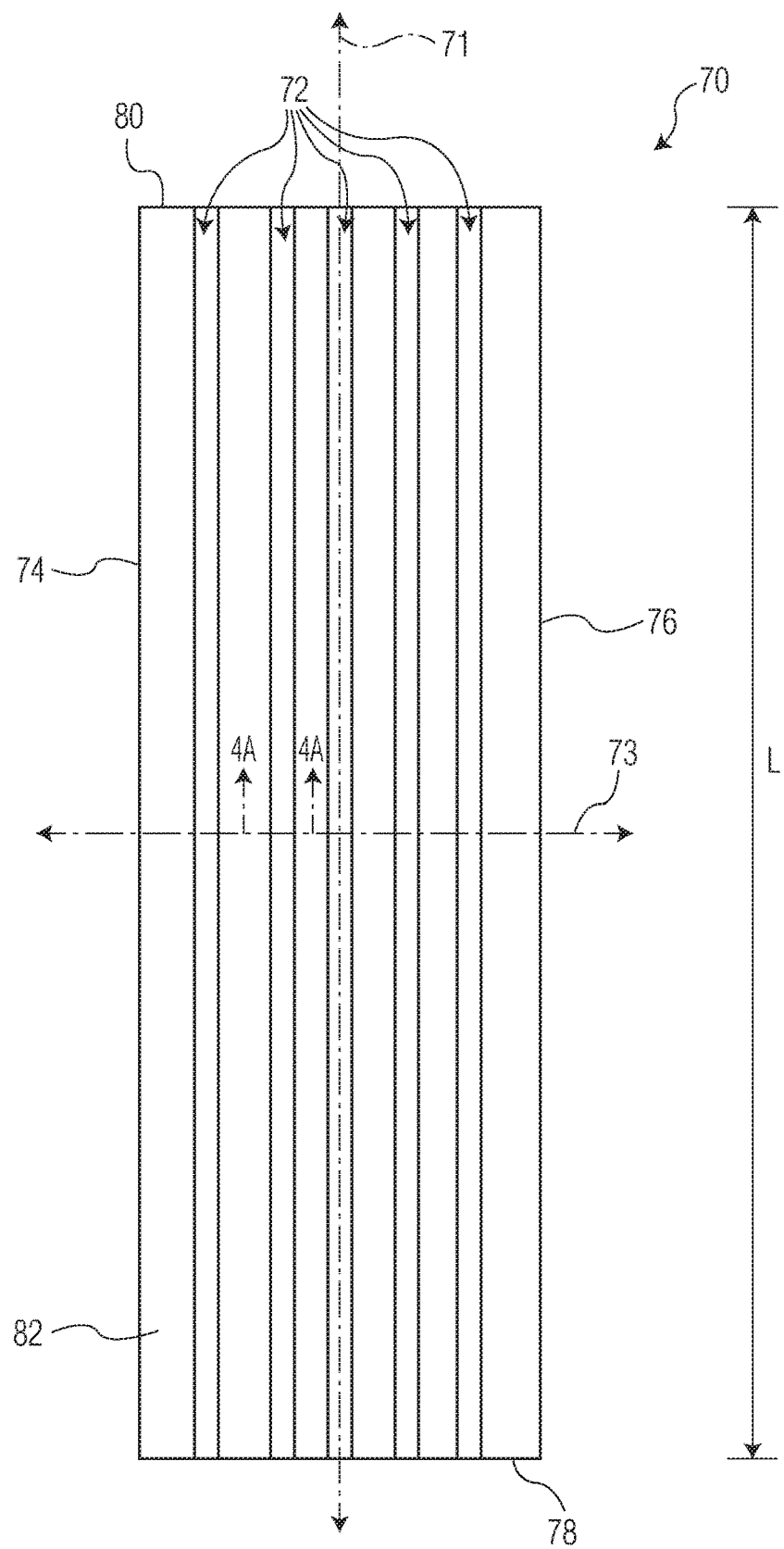
FIG. 3 is a top plan view of the material of the embodiment illustrated in FIGS. 1 and 2.

Distribution Material:

The distribution material 70 can preferably be disposed between the absorbent body 34 and the outer cover 26, as shown in FIGS. 2 and 5. As best illustrated in FIG. 3, the distribution material 70 can include a first side edge 74 and a second side edge 76 opposite from the first side edge 74. The distribution material 70 can also include a first end edge 78 and a second end edge 80. The second end edge 80 can be opposite from the first end edge 78. The distribution material 70 can include a first surface 82 and a second surface 84 opposite from the first surface 82. A distance between the first surface 82 and the second surface 84 can define a thickness 86 of the distribution material 70. The distance between the first surface 82 and the second surface 84 defining the thickness 86 of the distribution material 70 can be measured along a line that is perpendicular to a plane defined by the longitudinal axis 71 and the lateral axis 73 of the distribution material 70.

As illustrated in FIGS. 3, 4A, 4B, and 4D, at least one of the first surface 82 and the second surface 84 of the distribution material 70 can include at least one channel 72. Preferably, the distribution material 70 includes a plurality of channels 72 on at least one of the first surface 82 and the second surface 84. For example, the embodiment of the distribution material 70 depicted in FIGS. 3 and 4A includes five channels 72. In some embodiments, the distribution material 70 can include at least five, or at least ten, or at least twenty channels 72. In some embodiments, the distribution material 70 can include at least twenty-five channels 72. Of course, it is contemplated that in some embodiments the distribution material can include more than twenty-five channels 72. In some embodiments including a plurality of channels 72, a majority of the plurality of channels 72 can be configured substantially the same. In other embodiments including a plurality of channels 72, the channels 72 can be configured differently from one another.

Figure 4A:
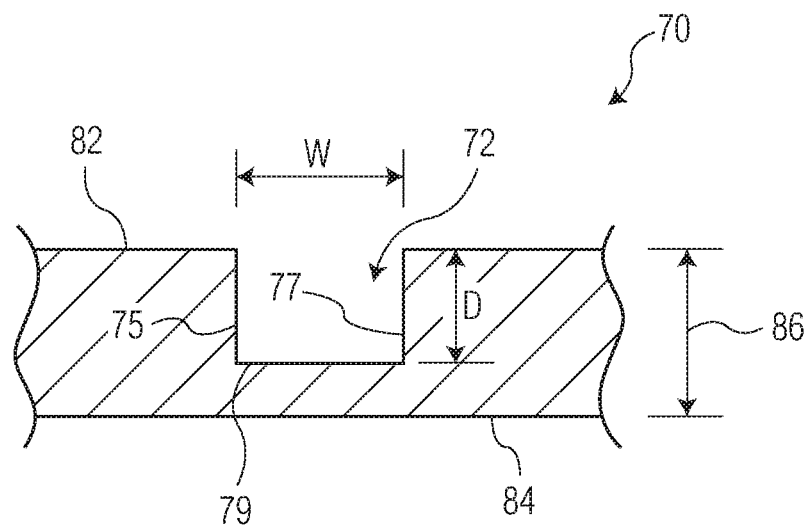
FIG. 4A is a detailed cross-sectional view of a portion of the material taken along line 4A-4A from FIG. 3.
Figure 4B:
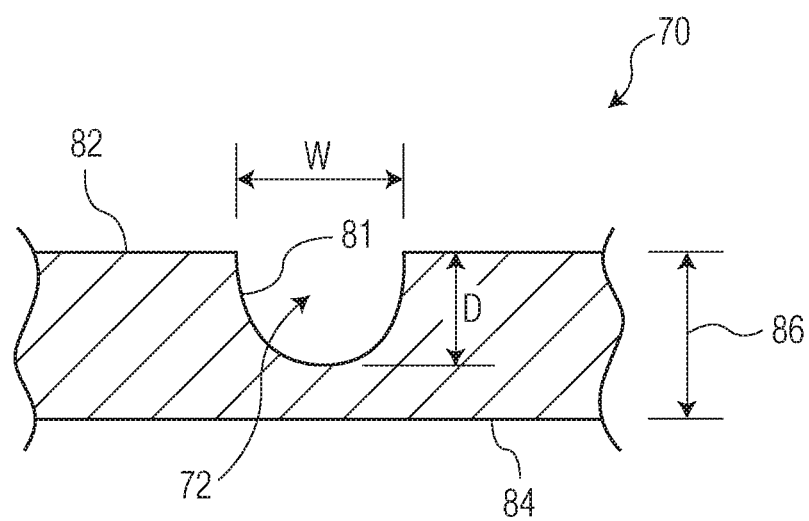
FIG. 4B is a detailed cross-sectional view similar to FIG. 4A, but of a material including an alternative channel cross-sectional shape.

As depicted in the cross-sectional image of FIG. 4A, some embodiments of channels 72 can be configured such that the channel 72 can include a distinct first sidewall 75 and a distinct second sidewall 77 opposite from the first sidewall 75. Some embodiments of a channel 72 can also include a distinct bottom wall 79 that spans between the first sidewall 75 and the second sidewall 77. Of course, it is contemplated that in other embodiments, a channel 72 could be configured to have a different cross-sectional shape, such as a semicircle as shown in FIG. 4B, that does not include a distinct first sidewall 75, second sidewall 77, or bottom surface 79, but has a single surface 81 providing the inner dimensionality to the channel 72. It is also contemplated that the channel 72 could be configured to include more than three surfaces providing the inner dimensionality to the channel 72. It is to be noted that the present disclosure is not limited to a particular cross-sectional shape of a channel 72, and is intended to encompass a variety of such cross-sectional shapes.

A channel 72 of the distribution material 70 can include a channel length L, a channel width W, and a channel depth D. In preferred embodiments, the channel 72 can extend in a direction substantially parallel to the longitudinal axis 71 of the distribution material 70. In some embodiments, the channel 72 can extend in a direction substantially parallel to the longitudinal axis 35 of the absorbent body 34. However, it is to be appreciated that a channel 72 need not be linear in nature, but could be sinusoidal, or any other suitable shape, in extending along its channel length L.

As depicted in FIG. 3, the channel length L is to be defined in the direction of the greatest length of the channel 72. For example, in the embodiment depicted in FIG. 3, the channel length L can be measured in a direction parallel to the longitudinal axis 71 of the distribution material 70. In some embodiments, the channel 72 can be configured such that the channel length L can be the same length as an overall length of the distribution material 70, such that the channel 72 extends from the first end edge 78 to the second end edge 80 of the distribution material 70. Such a configuration may be particularly beneficial where the distribution material 70 is a film and the channel 72 is formed through the extrusion process of manufacturing the distribution material 70. However, it is to be appreciated that the channel 72 can be configured such that the channel length L need not be the same length as the overall length of the distribution material 70. In some embodiments, the overall length of the distribution material 70 can be less than or equal to the overall length of the absorbent body 34, as illustrated in FIG. 2. In some embodiments where the distribution material 70 is used in an absorbent article 10, the channel length L can preferably be equal to or less than an overall length of the absorbent body 34. In some embodiments, the channel length L of the channel 72 can be greater than the overall length of the absorbent body 34. In some embodiments, the channel length L can range from 1.5 mm to 750 mm, and more preferably from 25 mm to 650 mm, and more preferably from 50 mm to 500 mm. Of course, in other embodiments, the channel length L can be outside these exemplary ranges.

A channel 72 of the distribution material 70 can include a channel width W. Regardless of the cross-sectional shape of the channel 72, the channel width W is to be defined as the greatest width of the channel 72 as measured along a line parallel to the lateral axis 73 of the distribution material 70. In some preferred embodiments, such as the embodiments illustrated in FIGS. 4A and 4B, the greatest width of the channel 72 defining the channel width W can be located at the top of the channel 72 along the plane of the surface of the distribution material 70 that includes the channel 72, such as the first surface 82 in FIGS. 4A and 4B. It is contemplated, however, that the greatest width of the channel 72 defining the channel width W could be located at a different depth plane of the channel 72, depending on the cross-sectional shape of the channel 72. In some embodiments, the channel width W is from 0.1 mm to 2.5 mm. In some embodiments, the channel width W of the channel 72 is from 0.2 mm to 2.0 mm.

Figure 4C:
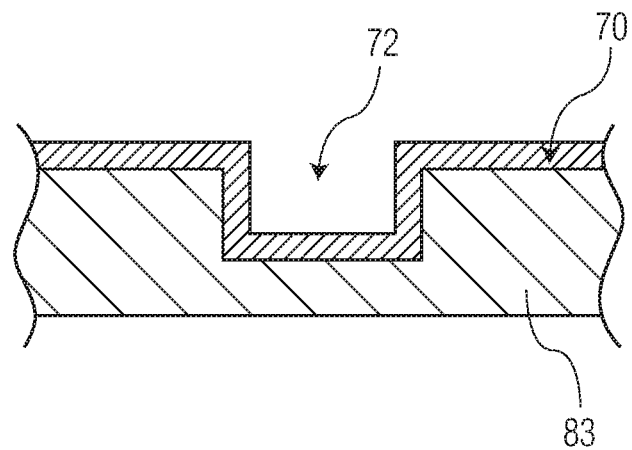
FIG. 4C is a detailed cross-sectional view similar to FIGS. 4A and 4B, but of a material including an alternative channel formed from an alternative manufacturing technique.
Figure 4D:
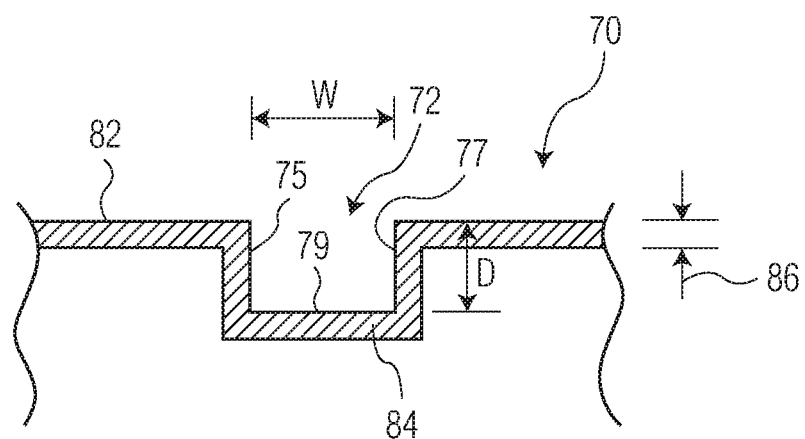
FIG. 4D is a detailed cross-sectional view similar to FIG. 4C, but with the sacrificial layer removed.

A channel 72 of the distribution material 70 can also include a channel depth D. Regardless of the cross-sectional shape of the channel 72, the channel depth D is to be defined as the greatest depth of the channel 72 as measured along a line perpendicular to the plane defined by the longitudinal axis 71 and the lateral axis 73 of the distribution material 70. The channel depth D does not extend completely through the distribution material 70, meaning that the channel depth D does not extend from the first surface 82 to the second surface 84. As such, the channel 72 does not allow a liquid to pass through the distribution material 70 from the first surface 82 to the second surface 84, or vice versa. For example, as illustrated in FIGS. 4A and 4B, the channel 72 is provided in the first surface 82 of the distribution material 70 and extends a channel depth D towards the second surface 84 of the distribution material 70, but does not extend completely to the second surface 84. In some embodiments, such as the embodiments depicted in FIGS. 4A and 4B, the channel depth D is less than the thickness 86 of the distribution material 70. However, in some embodiments, such as illustrated in FIGS. 4C and 4D, the channel 72 in the distribution material 70 can be configured to have a channel depth D that is greater than the thickness 86 of the distribution material 70. The channel 72 in the distribution material 72 as illustrated in FIG. 4D can be formed when the distribution material 70 is formed in conjunction with a sacrificial layer 83 (as depicted in FIG. 4C), and when the sacrificial layer 83 is removed (as depicted in FIG. 4D), the channel 72 can be configured to have a channel depth D that is greater than the thickness 86 of the distribution material 70. In some embodiments, the channel depth D of the channel 72 ranges from 0.5 mm to 1.5 mm. Of course, in other embodiments, the channel depth D may be outside of this exemplary range.

The distribution material 70 is preferably a liquid impermeable material. By being composed of a liquid impermeable material, the distribution material 70 can help distribute fluid along the length L of the channel 72 rather than allowing fluid to pass through the distribution material 70 in a direction perpendicular to the plane defined by the longitudinal axis 71 and lateral axis 73 of the distribution material 70. In some embodiments, the distribution material 70 can be configured as a film. Some preferable materials that such a film can include can be polypropylene, polyethylene, polyethylene terephthalate, polylactic acid, ethylene vinyl acetate. When the distribution material 70 is configured as a film, the channel(s) 72 can be configured in at least one of the first surface 82 and the second surface 84 during an extrusion process of the film. Alternatively, the channel(s) 72 could be configured in the distribution material 70 as a secondary step in a manufacturing process for making the distribution material 70. For example, the channel(s) 72 could be configured in the distribution material 70 by applying heat and/or pressure across the distribution material 70 after the material 70 has already been formed. Alternatively, the channel(s) 72 could be configured through the use of a sacrificial layer 83, as discussed above and as illustrated in FIG. 4C. It is contemplated that the channel(s) 72 can be configured in the distribution material 70 through any other suitable manufacturing technique.

In some embodiments, the distribution material 70 can be a separate component of the absorbent article 10, such as depicted in the embodiments illustrated in FIGS. 1-4A and 5. However, it is also contemplated that the distribution material 70 as described herein can form a portion of, or be part of, another component of the absorbent article 10. For example, it is to be appreciated that the distribution material 70 including at least one channel 70 can form a portion of, or be part of, the outer cover 26 of the absorbent article 10. As described above, in some embodiments the distribution material 70 as described herein can be the liquid impermeable inner layer 26b of the outer cover 26 (or the liquid impermeable outer cover 26 where the outer cover 26 is of a single-layer construction).

It has been found that the distribution material 70 including a channel 72 as described herein can help distribute fluids along the length L of the channel 72. As shown in the embodiment depicted in FIGS. 1-4A and 5, the distribution material 70 can be located beneath the absorbent body 34 such that the first surface 82 of the distribution material 70 that includes the channels 72 is disposed closer to the bottom surface 41 of the absorbent body 34 than the first surface 82 of the distribution material 70 is from the top surface 39 of the absorbent body 34. In such a configuration, the distribution material 70 can provide enhanced fluid transfer benefits for the absorbent article 10 by transferring fluid that has passed through one location of the absorbent body 34 and to the distribution material 70 to a different location of the absorbent body 34 by being distributed through the channels 72. For example, if a wearer insults the absorbent body 34 in a crotch region 16 of the absorbent article 10, fluid could pass through the absorbent body 34 in the crotch region 16 to the distribution material 70 such that the channel(s) 72 of the distribution material 70 could distribute the fluid to the absorbent body 34 in the front waist region 12 and/or the rear waist region 14. By further distributing the fluid, the fluid could be more quickly absorbed by the absorbent material in the absorbent body 34 in the front waist region 12 and/or the rear waist region 14. In such a context, the insulted area of the absorbent body 34 that has a higher amount of absorbed fluid can be serving as a fluid reservoir for the channel(s) 72 in the distribution material 70 to help distribute fluid to an area of the absorbent body 34 that has absorbed less fluid and can serve as an absorbent sink.

In particular, the distribution material 70 can provide enhanced fluid transfer benefits of fluid after the channel 72 already has fluid within the channel 72, or in other words, when the channel 72 is "primed." It has been discovered that the distribution material 70 with a channel 72 as described herein that is primed can provide a fluid mass flowrate of two to three times faster than when the channel 72 does not include any fluid. Thus, in embodiments where the distribution material 70 is employed in an absorbent article 10, the distribution material 70 can significantly increase the speed of fluid distribution along the length L of the channel 72 when a wearer has a second or subsequent insult in which fluid is already disposed within the channel 72. Additionally, it was observed that by having an absorbent sink (e.g., an area of the absorbent body 34 that has a lower comparative amount of fluid) that can accept fluid from a fluid reservoir (e.g., an area of the absorbent body 34 that has a higher comparative amount of fluid), the absorbent sink can allow the distribution material 70 to increase the speed of fluid distribution by two to twenty times as compared to if there is no absorbent sink to which the fluid can be distributed.

By distributing fluid from areas of the absorbent body 34 that have a high amount of fluid to areas of the absorbent body 34 that have lower amounts of fluid, a more efficient use of the absorbent body 34 can be realized. As a result, an absorbent body 34 may be designed to have less absorbent material, and the distribution material 70 can lead to material savings in forming the absorbent body 34 as well as a thinner absorbent body 34 that can provide enhanced fit and mobility benefits. Additionally, this distribution of fluid by the fluid distribution material 70 can help prevent pooling of fluids in the absorbent article 10, which can help reduce the likelihood that such fluid may leak from the absorbent article 10. Preventing the pooling of fluids in the absorbent article 10 can also help to keep the wearer's skin more dry.

Bodyside Liner:

The bodyside liner 28 of the absorbent article 10 can overlay the absorbent body 34 and the outer cover 26 and can be configured to receive insults of exudates from the wearer and can isolate the wearer's skin from liquid waste retained by the absorbent body 34. The bodyside liner 28 can from at least a part of the body facing surface 19 of the chassis 11.

In various embodiments, a fluid transfer layer 46 can be positioned between the bodyside liner 28 and the absorbent body 34 (as shown in FIG. 5). In various embodiments, an acquisition layer 48 can be positioned between the bodyside liner 28 and the absorbent body 34 or a fluid transfer layer 46, if present (as shown in FIG. 5). In various embodiments, the bodyside liner 28 can be bonded to the acquisition layer 48, or to the fluid transfer layer 46 if no acquisition layer 48 is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer 48, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. In some embodiments, the bodyside liner 28 and the outer cover 26 may be of the same dimensions in width and length. In some embodiments, however, the bodyside liner 28 may be narrower than the outer cover 26 and/or shorter than the outer cover 26. In some embodiments, the length of the bodyside liner 28 can range from 50%-100% of the length of the absorbent article 10 as measured in a direction parallel to the longitudinal axis 29. In some embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material.

The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentangled. The projection layer can include hollow projections, such as those disclosed in U.S. Pat. No. 9,474,660 invented by Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Containment Flaps:

In an embodiment, the absorbent article 10 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10 through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art.

In embodiments where the containment flaps 50, 52 are coupled to the chassis 11, the containment flaps 50, 52 can be bonded to the bodyside liner 28, the outer cover 26, or another layer, such as a spacer layer, if present, with a barrier adhesive, as is known in the art. Of course, the containment flaps 50, 52 can be bonded to other components of the chassis 11 and can be bonded with other suitable means other than a barrier adhesive. For example, the containment flaps 50, 52 can be bonded to the bodyside liner 28, the outer cover 26, or another layer with pressure bonding, thermal bonding, or ultrasonic bonding. The containment flaps 50, 52 can be constructed of a fibrous material which can be similar to the material forming the bodyside liner 28. Other conventional materials, such as polymer films, can also be employed.

As illustrated in FIG. 5, the containment flaps 50, 52 can each include a base portion 64 and a projection portion 66. The base portion 64 can be bonded to the chassis 11, for example, to the bodyside liner 28 or the outer cover 26 as mentioned above. The base portion 64 could be bonded to other components of the chassis 11. The projection portion 66 can be configured to extend away from the body facing surface 19 of the chassis 11 (such as the body facing surface 55 of the bodyside liner 28) at least in the crotch region 16 when the absorbent article 10 is in a relaxed configuration, as illustrated in FIG. 5.

It is contemplated that the containment flaps 50, 52 can be of various configurations and shapes, and can be constructed by various methods. For example, the containment flaps 50, 52 of FIGS. 2 and 5 depict a vertical containment flap 50, 52 that can be tacked down in both the front and rear waist regions 12, 14 where the projection portion 66 of each containment flap 50, 52 is tacked down to the bodyside liner 28 towards the longitudinal axis 29 of the absorbent article 10. However, it is contemplated that the containment flaps 50, 52 can be tacked down where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. patent Application Publication 2014/0350504. Such a configuration can also include the projection portions 66 being tacked down in either or both of the front and rear waist regions 12, 14, respectively. Of course, other configurations of containment flaps 50, 52 can be used in the absorbent article 10 and still remain within the scope of this disclosure.

The containment flaps 50, 52 can include one or more flap elastic members 68, such as the two flap elastic strands depicted in FIG. 5. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 5, can have two strands of elastomeric material extending longitudinally in the projection portion 66 of the containment flaps 50, 52, in generally parallel, spaced relation with each other. The flap elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration. Such an upright orientation of the projection portion 66 of containment flap 50 and the projection portion 66 of containment flap 52 is illustrated in FIG. 5, where the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. In one embodiment, the elastic members 68 can be coated with adhesive while elongated to a specified length prior to attaching to the elastic members 68 to the containment flaps 50, 52. In this exemplary method of bonding the elastic members 68 to the containment flaps 50, 52, the portion of the elastic members 68 not coated with adhesive, will retract after the elastic members 68 and the absorbent article 10 are cut in manufacturing to form an individual absorbent article 10. As noted above, the relaxing of the elastic members 68 when the absorbent article 10 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 55 of the bodyside liner 28), as depicted in FIG. 5.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein in FIG. 2 each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10 without departing from the scope of this disclosure.

Waist Containment Member:

In an embodiment, the absorbent article 10 can have one or more waist containment members 54. FIGS. 1 and 2 illustrate a preferred embodiment of a waist containment member 54 on an absorbent article 10, such as a diaper where the waist containment member 54 can be disposed in the rear waist region 14. In some embodiments, the waist containment member 54 can be disposed in the front waist region 12. The waist containment member 54 can be disposed on the body facing surface 45 of the absorbent assembly 44. In some embodiments, such as in embodiments illustrated in FIGS. 1 and 2, the waist containment member 54 can be disposed on the body facing surface 55 of the bodyside liner 28. Additionally, in the absorbent article 410 in FIGS. 9 and 10, the waist containment member 54 can be disposed on the rear waist panel 15. The waist containment member 54 can be coupled to the chassis 11 such that a portion of the waist containment member 54 is free to move with respect to the chassis 11 and can form a pocket to help contain body exudates.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. In some embodiments, the waist containment member 54 can include an elastic material to provide additional fit and containment properties to the absorbent article 10. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist containment member 54 may be omitted from the absorbent article without departing from the scope of this disclosure.

Fastening System:

In an embodiment, the absorbent article 10 can include a fastening system. The fastening system can include one or more back fasteners 91 and one or more front fasteners 92. The embodiments shown in FIGS. 1 and 2 depict an embodiment with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

Embodiments

Embodiment 1: A material comprising: a first side edge; a second side edge opposite from the first side edge; a first end edge; a second end edge opposite from the first end edge; a first surface; and a second surface opposite from the first surface, a distance between the first surface and the second surface defining a thickness of the material; wherein the material is liquid impermeable and at least one of the first surface and the second surface comprise at least one channel, the at least one channel comprising: a channel width, the channel width being from 0.1 mm to 2.5 mm; a channel length; a channel depth, the channel depth being configured such that the channel does not extend completely through the material.

Embodiment 2: The material of embodiment 1, wherein the material comprises a plurality of channels.

Embodiment 3: The material of embodiment 2, wherein a majority of the plurality of channels are configured substantially the same as the at least one channel.

Embodiment 4: The material of any of the preceding embodiments, wherein the channel depth is 0.5 mm to 1.5 mm.

Embodiment 5: The material of any of the preceding embodiments, wherein the channel length is 1.5 mm to 750 mm.

Embodiment 6: The material of any of the preceding embodiments, wherein the material is a film.

Embodiment 7: The material of any of embodiment 6, wherein the film comprises a polymer, the polymer being selected from the group consisting of: polyethylene or polypropylene, polyethylene terephthalate, polylactic acid, and ethylene vinyl acetate.

Embodiment 8: The material of any one of the preceding embodiments, wherein the channel length of the at least one channel extends from the first end edge to the second end edge of the material.

Embodiment 9: An absorbent assembly comprising: an absorbent body comprising: absorbent material; a first end edge; a second end edge opposite from the first end edge; a pair of longitudinal side edges; a top surface; and a bottom surface opposite from the top surface; a material, the material being liquid impermeable and comprising: a first side edge; a second side edge opposite from the first side edge; a first end edge; a second end edge opposite from the first end edge; a first surface; and a second surface opposite from the first surface, a distance between the first surface and the second surface defining a thickness of the material; wherein the first surface comprises at least one channel, the at least one channel comprising: a channel width; a channel length; and a channel depth, the channel depth being configured such that the channel does not extend completely through the material.

Embodiment 10: The absorbent assembly of embodiment 9, wherein the channel width is from 0.1 mm to 2.5 mm.

Embodiment 11: The absorbent assembly of embodiment 9 or 10, wherein the channel depth is 0.5 mm to 1.5 mm.

Embodiment 12: The absorbent assembly of any one of embodiments 9-11, wherein the material comprises a plurality of channels, wherein a majority of the plurality of channels are configured substantially the same as the at least one channel.

Embodiment 13: The absorbent assembly of any one of embodiments 9-12, wherein the first surface of the material is disposed closer to the bottom surface of the absorbent body than the first surface of the material is from the top surface of the absorbent body.

Embodiment 14: The absorbent assembly of any one of embodiments 9-13, wherein the absorbent body further comprises a longitudinal axis and a lateral axis, and wherein the at least one channel extends in a direction substantially parallel to the longitudinal axis of the absorbent body.

Embodiment 15: The absorbent assembly of any one of embodiments 9-14, wherein the material is a film.

Embodiment 16: An absorbent article comprising: a bodyside liner; an absorbent body, the absorbent body comprising: absorbent material; a front end edge; a rear end edge, the rear end edge opposed from the front end edge; and a pair of longitudinal side edges; and a material, the absorbent body being disposed between the bodyside liner and the material, the material being liquid impermeable and comprising: a first side edge; a second side edge opposite from the first side edge; a first end edge; a second end edge opposite from the first end edge; a first surface; and a second surface opposite from the first surface, a distance between the first surface and the second surface defining a thickness of the material; wherein the first surface comprises a plurality of channels, the plurality of channels each comprising: a channel width; a channel length; and a channel depth, the channel depth being configured such that the channel does not extend completely through the material.

Embodiment 17: The absorbent article of embodiment 16, wherein the channel width is from 0.1 mm to 2.5 mm and the channel depth is 0.5 mm to 1.5 mm.

Embodiment 18: The absorbent article of embodiment 16 or 17, wherein the material is a film.

Embodiment 19: The absorbent article of any one of embodiments 16-18, further comprising an outer cover, wherein the material is disposed between the outer cover and the absorbent body.

Embodiment 20: The absorbent article of any one of embodiments 16-18, further comprising an outer cover, wherein the material forms at least a portion of an outer cover.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A material comprising:
   a first side edge;
   a second side edge opposite from the first side edge;
   a first end edge;
   a second end edge opposite from the first end edge;

a first surface; and
a second surface opposite from the first surface, a distance between the first surface and the second surface as measured along a line that is perpendicular to a plane defined by a longitudinal axis and a lateral axis of the material defining a thickness of the material;
wherein the material is liquid impermeable and at least one of the first surface and the second surface comprise at least one channel, the at least one channel comprising:
a channel width, the channel width being from 0.5 mm to 2.5 mm;
a channel length;
a channel depth, the channel depth being configured such that the channel does not extend completely through the material, and wherein the channel depth is greater than the thickness of the material, wherein the channel depth is a greatest depth of the channel as measured along the line perpendicular to the plane defined by the longitudinal axis and the lateral axis of the material.

2. The material of claim 1, wherein the material comprises a plurality of channels.

3. The material of claim 2, wherein a majority of the plurality of channels are configured substantially the same as the at least one channel.

4. The material of claim 1, wherein the channel depth is 0.5 mm to 1.5 mm.

5. The material of claim 1, wherein the channel length is 1.5 mm to 750 mm.

6. The material of claim 1, wherein the material is a film.

7. The material of claim 6, wherein the film comprises a polymer, the polymer being selected from the group consisting of: polyethylene or polypropylene, polyethylene terephthalate, polylactic acid, and ethylene vinyl acetate.

8. The material of claim 1, wherein the channel length of the at least one channel extends from the first end edge to the second end edge of the material.

9. An absorbent assembly comprising:
an absorbent body comprising:
absorbent material;
a first end edge;
a second end edge opposite from the first end edge;
a pair of longitudinal side edges;
a top surface; and
a bottom surface opposite from the top surface;
a material, the material being liquid impermeable and comprising:
a first side edge;
a second side edge opposite from the first side edge;
a first end edge;
a second end edge opposite from the first end edge;
a first surface; and
a second surface opposite from the first surface, a distance between the first surface and the second surface as measured along a line that is perpendicular to a plane defined by a longitudinal axis and a lateral axis of the material defining a thickness of the material;
wherein the first surface comprises at least one channel, the at least one channel comprising:
a channel width, the channel width being from 0.5 mm to 2.5 mm;
a channel length; and
a channel depth, the channel depth being configured such that the channel does not extend completely through the material, and wherein the channel depth is greater than the thickness of the material, wherein the channel depth is a greatest depth of the channel as measured along the line perpendicular to the plane defined by the longitudinal axis and the lateral axis of the material.

10. The absorbent assembly of claim 9, wherein the channel width is from 0.5 mm to 2.0 mm.

11. The absorbent assembly of claim 9, wherein the channel depth is 0.5 mm to 1.5 mm.

12. The absorbent assembly of claim 9, wherein the material comprises a plurality of channels, wherein a majority of the plurality of channels are configured substantially the same as the at least one channel.

13. The absorbent assembly of claim 9, wherein the first surface of the material is disposed closer to the bottom surface of the absorbent body than the first surface of the material is from the top surface of the absorbent body.

14. The absorbent assembly of claim 9, wherein the absorbent body further comprises a longitudinal axis and a lateral axis, and wherein the at least one channel extends in a direction substantially parallel to the longitudinal axis of the absorbent body.

15. The absorbent assembly of claim 9, wherein the material is a film.

16. An absorbent article comprising:
a bodyside liner;
an absorbent body, the absorbent body comprising:
absorbent material;
a front end edge;
a rear end edge, the rear end edge opposed from the front end edge; and
a pair of longitudinal side edges; and
a material, the absorbent body being disposed between the bodyside liner and the material, the material being liquid impermeable and comprising:
a first side edge;
a second side edge opposite from the first side edge;
a first end edge;
a second end edge opposite from the first end edge;
a first surface; and
a second surface opposite from the first surface, a distance between the first surface and the second surface as measured along a line that is perpendicular to a plane defined by a longitudinal axis and a lateral axis of the material defining a thickness of the material;
wherein the first surface comprises a plurality of channels, the plurality of channels each comprising:
a channel width, the channel width being from 0.5 mm to 2.5 mm;
a channel length; and
a channel depth, the channel depth being configured such that the channel does not extend completely through the material, and wherein the channel depth is greater than the thickness of the material, wherein the channel depth is a greatest depth of the channel as measured along the line perpendicular to the plane defined by the longitudinal axis and the lateral axis of the material.

17. The absorbent article of claim 16, wherein the channel depth is 0.5 mm to 1.5 mm.

18. The absorbent article of claim 16, wherein the material is a film.

19. The absorbent article of claim 16, further comprising an outer cover, wherein the material is disposed between the outer cover and the absorbent body.

20. The absorbent article of claim 16, further comprising an outer cover, wherein the material forms at least a portion of the outer cover.

* * * * *